US00PP37166P2

(12) United States Plant Patent
Capo

(10) Patent No.: US PP37,166 P2
(45) Date of Patent: Dec. 23, 2025

(54) ***PETUNIA* PLANT NAMED 'KLEPH24698'**

(50) Latin Name: ***Petunia* x *atkinsiana* (syn. P. x *hybrida*)**
Varietal Denomination: KLEPH24698

(71) Applicant: KLEMM + SOHN GMBH & CO. KG, Stuttgart (DE)

(72) Inventor: Antonella Capo, Latina (IT)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/247,548

(22) Filed: Jun. 24, 2025

(51) Int. Cl.
*A01H 5/02* (2018.01)
*A01H 6/82* (2018.01)

(52) U.S. Cl.
USPC ..... Plt./356.15
CPC ..... *A01H 6/824* (2018.05)

(58) Field of Classification Search
USPC ..... Plt./356.15
CPC ..... A01H 5/02
See application file for complete search history.

*Primary Examiner* — Kent L Bell
(74) *Attorney, Agent, or Firm* — Weatherly IP Solutions, LLC; James M. Weatherly

(57) ABSTRACT

A new *Petunia* plant particularly distinguished by large white flowers; and a trailing to semi-trailing plant habit. is disclosed.

1 Drawing Sheet

Genus and species: *Petunia* x *atkinsiana* (syn. *P.* x *hybrida*).
Variety denomination: 'KLEPH24698'.

BACKGROUND OF THE NEW PLANT

The present invention comprises a new and distinct variety of *Petunia*, botanically known as *Petunia* x *atkinsiana* (syn. *P.* x *hybrida*) and hereinafter referred to by the variety name 'KLEPH24698'. 'KLEPH24698' is a selection from a controlled cross between the proprietary female *Petunia* line *Petunia* 'PH-2018-4359' (unpatented) and the male *Petunia* line 'PH-2018-4389' (unpatented).

In July of 2019, the proprietary female *Petunia* line 'PH-2018-4359' and the proprietary male *Petunia* line 'PH-2018-4389' were cross pollinated in Latina, Italy and seeds were obtained. The seeds were sown and plants were grown for evaluation. A plant line was selected in April 2020 in Latina, Italy and named 'KLEPH24698'. In May 2020, 'KLEPH24698' was first vegetatively propagated by terminal tip cuttings and tissue culture in Latina, Italy. 'KLEPH24698' was found to reproduce true to type in successive generations of asexual propagation via tissue culture and terminal tip cuttings.

SUMMARY

The following are the most outstanding and distinguishing characteristics of this new variety when grown under normal horticultural practices in Latina, Italy.

1. Large white flowers; and
2. Trailing to semi-trailing plant habit.

DESCRIPTION OF THE PHOTOGRAPH

This new *Petunia* plant is illustrated by the accompanying photograph, which shows flowers of the plant. The plant is about twenty-weeks-old grown in Stuttgart, Germany in August 2024. The colors shown are as true as can be reasonably obtained by conventional photographic procedures.

DESCRIPTION OF THE NEW VARIETY

The following detailed descriptions set forth the distinctive characteristics of 'KLEPH24698'. The data which define these characteristics were collected from asexual reproductions carried out in Latina, Italy. Data was collected on thirteen-week-old plants grown indoors in Latina, Italy under greenhouse conditions in May 2025. Color references are to The R.H.S. Colour Chart of The Royal Horticultural Society of London (R.H.S.), 5$^{th}$ edition (2007).

Classification:
- *Family*.—Solanaceae.
- *Species*.—*Petunia* x *atkinsiana* (syn. *P.* x *hybrida*).
- *Common name*.—*Petunia*.
- *Variety*.—'KLEPH24698'.

Parentage:
- *Female parent*.—*Petunia* 'PH-2018-4359' (unpatented).
- *Male parent*.—*Petunia* 'PH-2018-4389' (unpatented).

Plant:
- *Form and habit*.—Medium to high vigor, semi-trailing to trailing habit.
- *Height* (*from top of soil*).—20.0 cm.
- *Width* (*horizontal plant diameter*).—60.0 cm.
- *Propagation type*.—Vegetative by terminal tip cuttings and tissue culture.
- *Time to produce a finished flowering plant*.—About 12 weeks in winter under short day conditions, about 6.5 weeks in spring.
- *Time to initiate and develop roots*.—2 to 3 weeks.
- *Root description*.—Moderate density, moderate branching, white roots (RHS 155C).

Stems:

*Average number (basal).*—7.

*Length of basal branches (from the base of the stem to the tip).*—35.0 cm.

*Internode length.*—1.0 cm.

*Diameter of branches (from midpoint).*—0.3 cm.

*Stem color.*—RHS 144B.

*Anthocyanin.*—Absent.

*Texture.*—Pubescent.

Leaves:

*Arrangement.*—Alternate along the stem and opposite under the inflorescence.

*Length.*—Up to 5.0 cm.

*Width.*—2.5 cm.

*Shape.*—Elliptic.

*Apex.*—Slightly obtuse.

*Base.*—Attenuate.

*Margin.*—Entire.

*Immature leaf color.*—Upper surface: RHS 138A. Lower surface: RHS 138B.

*Mature leaf color.*—Upper surface: RHS 137B. Lower surface: RHS 138B.

*Texture.*—Upper surface: Pubescent. Lower surface: Pubescent.

*Venation pattern.*—Arcuate.

*Venation color.*—Upper surface: RHS 137B. Lower surface: RHS 145B.

*Petioles.*—Length: 0.4 cm. Diameter: 0.3 cm. Color: RHS 145A. Texture: Pubescent.

Flower bud:

*Shape.*—Irregularly oblong.

*Length.*—5.3 cm.

*Diameter.*—0.9 cm.

*Color at tight bud.*—RHS 2D.

*Texture.*—Pubescent.

Inflorescence:

*Blooming habit (flowering season).*—Continuously flowering during spring and summertime.

*Inflorescence type.*—Sympodial, with monochasial growth.

*Number of flowers per node.*—1.

*Lastingness of individual blooms on the plant.*—12 days.

*Fragrance.*—Absent.

*Flowers.*—Arrangement: Composed of 5 petals, fused at the base. Diameter (flower face): 7.0 cm. Depth (total length of flower): 6.5 cm. Throat/Funnel: Length: 3.0 cm. Diameter (at opening): 0.7 cm. Texture: Inner surface: Smooth. Outer surface: Pubescent. Color: Inner surface: RHS 149D. Outer surface: RHS 149D and veins RHS 149A. Petals: Color, mature flower (fully opened): Upper surface: RHS NN155D. Lower surface: RHS NN155D. Apex: Cuspidate. Base: Fused. Shape: Funnelform. Margin: Entire. Strength of waviness: Medium. Degree of lobation: Medium.

*Calyx arrangement.*—5 sepals fused at the base. Color: Upper surface: RHS 137B. Lower surface: RHS 137C. Length: 1.5 cm. Width: 0.3 cm. Shape: Linear. Apex: Acute. Base: Attenuate. Margin: Entire. Texture: Upper surface: Pubescent. Lower surface: Pubescent.

*Pedicels.*—Color: RHS 144A to RHS 144B. Length: 2.7 cm. Diameter: 0.15 cm. Texture: Pubescent.

Reproductive organs:

*Stamens.*—Quantity: 5. Shape: Needle with oblong head. Filament: Length: From 0.9 cm to 1.2 cm. Diameter: 0.01 cm. Color: RHS 157A. Anther: Shape: Oblong. Color: RHS 155A. Length: 0.2 cm. Diameter: 0.15 cm. Pollen: Color: RHS 158A. Amount: Sparse.

*Pistils.*—Quantity per flower: 1. Length: 2.5 cm. Stigma color: RHS 145B. Style color: RHS 145C.

Fruit and seed set: None observed.

Disease and pest/insect resistance: None observed.

COMPARISON WITH PARENTAL LINES AND KNOWN VARIETY

'KLEPH24698' is a distinct variety of *Petunia*. 'KLEPH24698' is distinguished from its parents as described in Table 1:

TABLE 1

Comparison with Parental Lines

| Characteristic | Subject Variety 'KLEPH24698' | Female parent | Male Parent |
|---|---|---|---|
| Flower size | Larger than the female and male parents | Smaller than 'KLEPH24698' | Smaller than 'KLEPH24698' |
| Growing habit | Semi-trailing to trailing | Mounding | Semi-trailing |

'KLEPH24698' is most similar to the commercial *Petunia* plant named Surfinia White 'Revolution White' (U.S. Plant Pat. No. 8,768) Differences between the two varieties are described in Table 2:

TABLE 2

Comparison with Similar Variety

| Characteristic | Subject Variety 'KLEPH24698' | Commercial line Surfinia White 'Revolution White' |
|---|---|---|
| Growing habit | Semi trailing to trailing | Very flat |
| Flower | Well open corolla with a pure white flower color | Closer to a funnel shaped corolla |
| Earliness | At least one week earlier: in average 12 weeks from potting to have a finished flowering plant in winter, under short day length, and 6.5 weeks in spring. | At least one week later: about 13 weeks in winter and 8 in spring. |

I claim:

1. A new and distinct variety of *Petunia* plant named 'KLEPH24698' as illustrated and described herein.

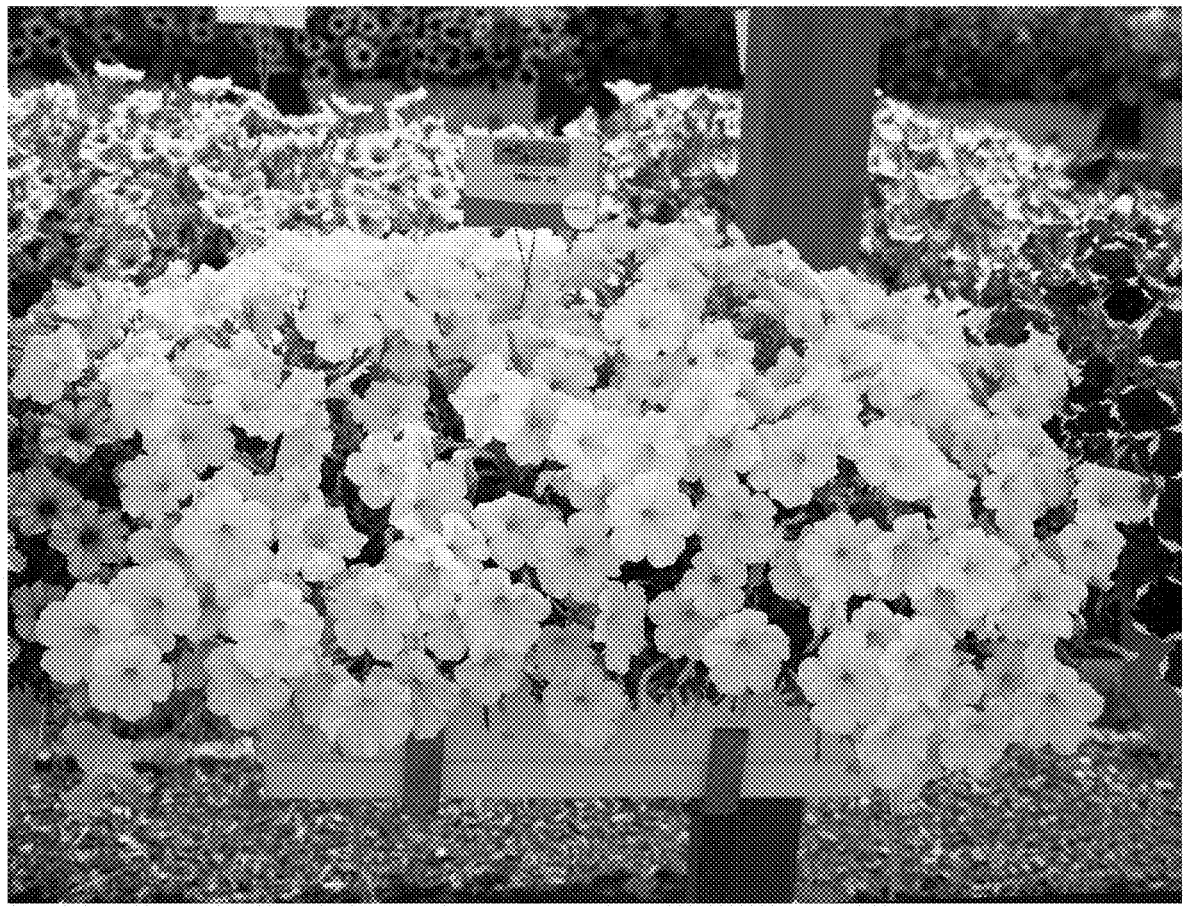

* * * * *